United States Patent [19]

Moorey

[11] 4,353,256

[45] Oct. 12, 1982

[54] NON-CONTACT MEASUREMENT OF PHYSICAL PROPERTIES OF CONTINUOUSLY MOVING METAL STRIP

[75] Inventor: Ernest J. Moorey, Chester, England

[73] Assignee: The Electricity Council, England

[21] Appl. No.: 225,926

[22] Filed: Jan. 19, 1981

[51] Int. Cl.³ ............................................. G01K 11/24
[52] U.S. Cl. ............................................. 73/597; 73/628
[58] Field of Search ...................... 73/597, 596, 628; 367/27, 32, 35

[56] References Cited

U.S. PATENT DOCUMENTS

| | | | |
|---|---|---|---|
| 3,375,897 | 4/1968 | Engle et al. | 367/27 |
| 3,720,098 | 3/1973 | Dixon | 73/597 |
| 3,782,177 | 1/1974 | Hoop | 73/596 |
| 4,073,007 | 2/1978 | Boivin | 73/597 |
| 4,291,577 | 9/1981 | Baum et al. | 73/597 |

*Primary Examiner*—Howard A. Birmiel

*Attorney, Agent, or Firm*—Beveridge, De Grandi & Kline

[57] ABSTRACT

A parameter representative of a physical property of a continuously moving metal strip is determined by repetitively generating acoustical shock waves, containing ultrasonic frequencies, and adjacent the strip and measuring the speed of transmission of the shock wave in the strip. An electric spark generator with a collimator feeds the acoustic energy to the strip 10 and four microphones arranged as a first pair on opposite sides of the strip spaced a known distance from a second pair also on opposite sides of the strip pick up the signal transmitted through the strip. The difference between the mean time of arrival at the first pair and the mean time of arrival at the second pair enables the velocity of propagation in the strip to be determined despite movements of the strip transverse to its plane. The velocity of propagation in particular may be used as a measure of Young's modulus and hence, in the case of a material such as aluminium, as a measure of the temperature of heat treatment.

11 Claims, 3 Drawing Figures

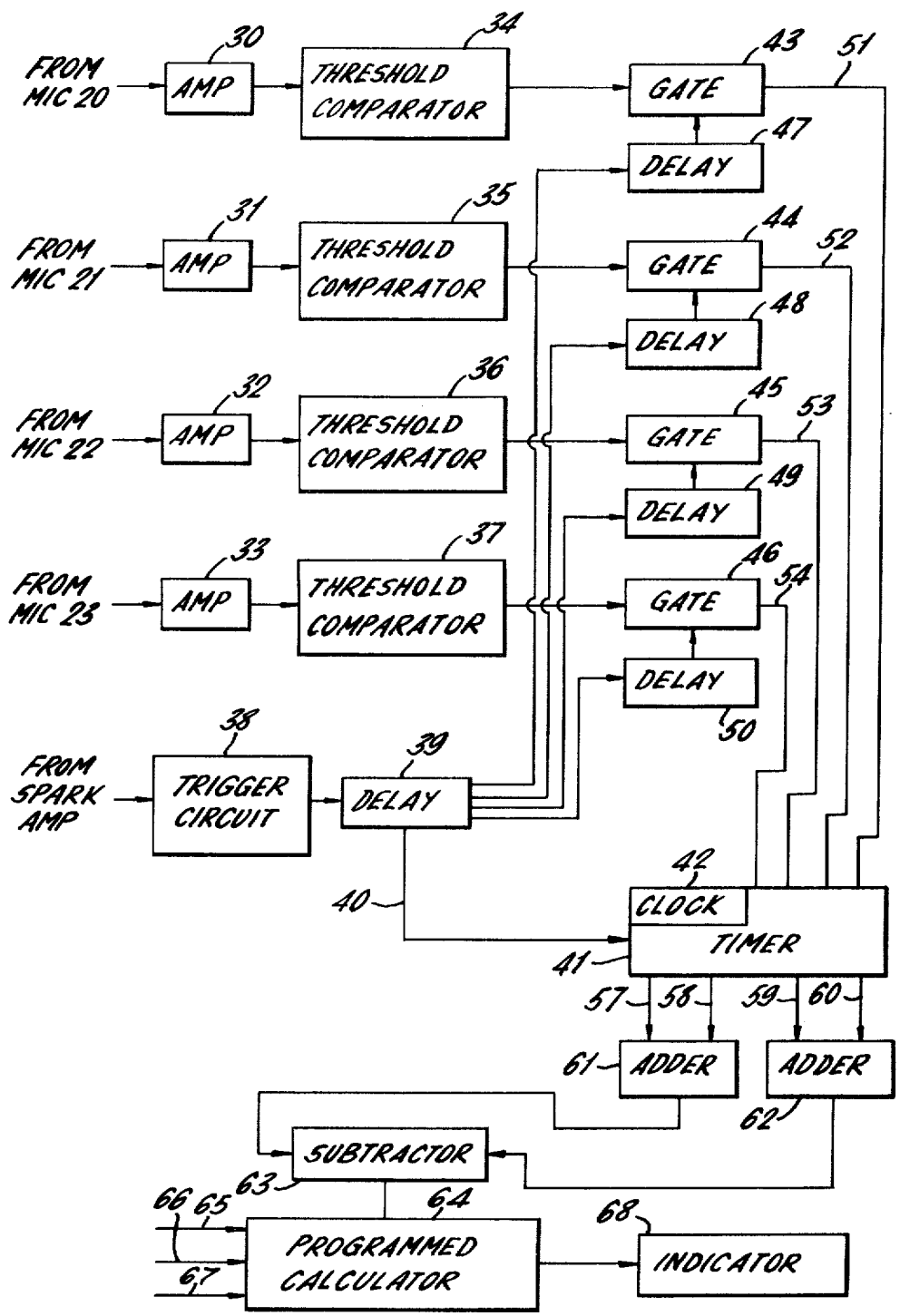

NON-CONTACT MEASUREMENT OF PHYSICAL PROPERTIES OF CONTINUOUSLY MOVING METAL STRIP

BACKGROUND OF THE INVENTION

1. Field of the Invention

This invention relates to methods of and apparatus for the measurement of physical properties of continuously moving metal strip without making physical contact with the moving strip.

2. Prior Art

As will be apparent from the following description, the technique of the present invention essentially makes a measurement of the velocity of an acoustic wave in the solid. This velocity is related to the Young's modulus of the material. The technique therefore may be used for measuring the Young's modulus. More widely however there are other physical properties of a material which can be determined from knowledge of the Young's modulus. In particular the Young's modulus varies with temperature and determination of Young's modulus enables the temperature of the material to be determined.

In U.S. Pat. No. 4,073,007, there is described a technique for measuring stress in a tensioned band of sheet metal, e.g. from a rolling mill, in which a disturbance is produced, e.g. by striking the band with a hammer, and the speed of propagation of the disturbance between spaced sensing locations is measured by eddy current detectors in which the effects of the disturbance on eddy currents are noted.

BRIEF SUMMARY OF THE INVENTION

The present invention provides a method of and apparatus for measurement on a moving metal strip, without physical contact with the strip, enabling a parameter such as Young's modulus to be determined despite movements of the strip transverse to its general plane. In the heat treatment of metals, for example in the treatment of continuous strip material, non-contact measurement of Young's modulus of a strip as it is being treated enables the state of annealing of the strip to be determined. The technique of the present invention leads to the possibility of monitoring the state of annealing of metal strip material as the material is being treated.

According to one aspect of the present invention a method of determining a parameter representative of a physical property of continuously moving strip metal comprises the steps of generating an acoustical shock wave, containing ultrasonic frequencies, near one location on the surface of the strip and measuring the time of transmission of the shock wave through the material between second and third locations to enable the velocity of propagation to be determined, wherein the time of arrival of the acoustic shock wave at each of said second and third locations in the material is determined by using, for each of said second and third locations, two microphones near but not in contact with opposite faces of the strip and determining the difference between the mean arrival times of the acoustic wave at the two microphones at the second and third locations. This velocity of propagation V is given by the expression $$V = \sqrt{\frac{E}{2(1 + \sigma)\rho}}$$

where
E is Young's modulus
$\sigma$ is Poisson's ratio, and
$\rho$ is the relative density For most materials it can be assumed that Poisson's ratio and the relative density will remain constant over the range of conditions for which measurements are to be made. The velocity of transmission is thus proportional to the square root of Young's modulus. Young's modulus is temperature-dependent and thus, other things being equal, measurement of the velocity of transmission enables the temperature of the material to be determined. Commonly, for any given system, the relationship between velocity of transmission and temperature can be determined empirically so that measurement apparatus can be calibrated.

This technique enables measurement to be made of a physical parameter of metal strip which is being processed. In such strip, the shock waves generated near one surface will be propagated along the length or across the width of the strip. It is readily possible to determine the time of arrival of a shock wave at distant points by means of microphones. Because the strip, in practical cases, often is moving transversely to its plane, two microphones adjacent opposite faces of the strip are used so that if the strip moves towards one microphone it moves away from the other. The average time of arrival of the impulse at the two microphones gives a mean time corresponding to that if the strip remained midway between the two microphones. Two such pairs of microphones are used, the two pairs being spaced apart so enabling the velocity of propagation between the two pairs to be determined. This removes any possible errors due to changes in the distance between the shock wave generator and the strip.

The shock wave contains ultrasonic frequencies and is conveniently produced by a short duration pulse having a rapid rise time, e.g. about 2 microseconds. Such a shock wave may be produced by an electric spark adjacent the material under test. Preferably the shock wave comprises a short duration pulse of ultrasonic energy. The electric spark may conveniently be arranged to produce regularly repetitive pulses.

According to another aspect of the invention, apparatus for determining a parameter representative of a physical property of continuously moving metal strip comprises a shock wave generator near one surface of the strip at one location for generating a shock wave containing ultrasonic frequencies and, at each of spaced second and third locations, two acoustic signal receivers near the strip but on opposite faces thereof and means responsive to the difference between the average time of receipt of the shock wave at the two receivers at the second location and the average time of receipt at the two receivers at the third location for determining the velocity of propagation of the acoustic wave signal between the second and third locations in the strip under test.

As indicated above, the shock wave generator conveniently comprises an electric circuit arranged to provide a short duration pressure pulse signal from a spark discharge. This pulse signal has a short rise time and thus contains ultrasonic energy. A collimator may be provided between the shock wave generator and said material to direct the shock wave onto a selected surface region of the material.

The receivers may each comprise a microphone near a surface of the material. It may be preferred to use directional microphones (e.g. a small ultrasonic receiver at the focus of a parabolic reflector or to provide a suitable collimator between the material and each microphone.

BRIEF DESCRIPTION OF THE DRAWINGS

FIG. 2 shows in further detail part of the apparatus used in carrying out the method illustrated in FIG. 1.

DESCRIPTION OF THE PREFERRED EMBODIMENT

Figure 1:
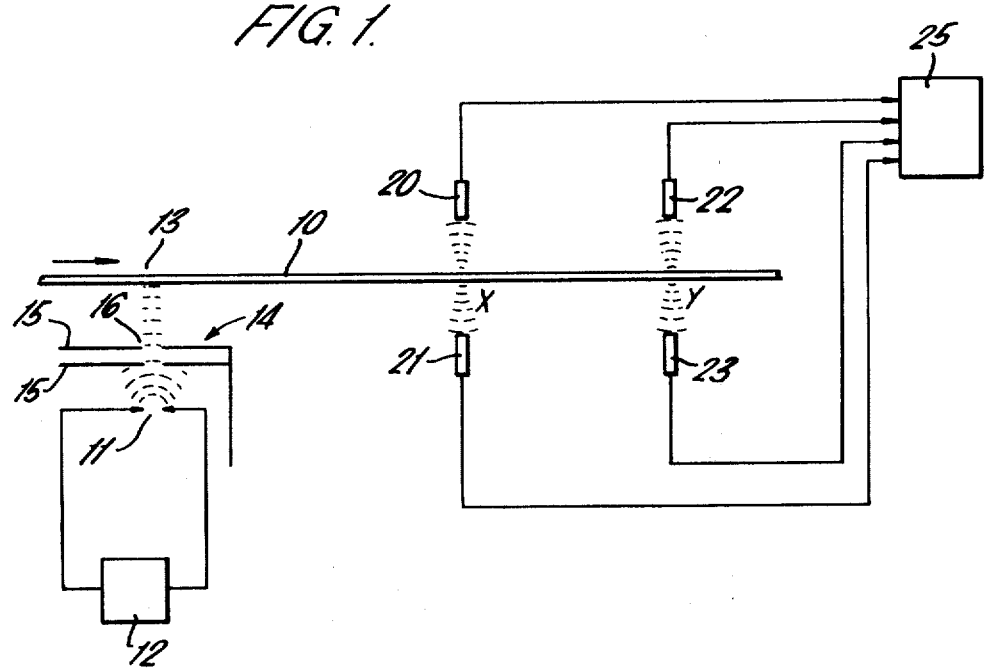
FIG. 1 shows diagrammatically one method of determining a parameter representative of a physical property of a moving metal strip.

Referring to FIG. 1 there is shown diagrammatically in side elevation a moving strip 10 of hot metal, for example a strip of sheet material which has been subjected to a heat treatment process such as annealing. Adjacent to this strip, an electric spark gap 11 is repetitively energised from a source 12 to produce a series of acoustic impulses, at a frequency, for example, of 50 Hz, which impinge on the strip at 13. The arc discharge across the gap has a very short voltage rise time, e.g. about 2 microseconds, and this will generate most of its energy as ultrasonic signals in the 100 kHz region. A collimator 14 may be provided to limit the area of the strip on which the ultrasonic impulses impinge. If such a collimator 14 is required, it may conveniently take the form of a series of plates 15, each having an aperture 16, the apertures being aligned to form the required path for the shock wave. Remote from the point 13 are a first pair of directional microphones 20, 21 directed towards opposite faces of the strip at a point X. Adjacent another point Y, spaced along the strip remote from X are a second pair of microphones 22, 23 also directed towards opposite faces of the strip. These microphones 20 to 23 are designed to be sensitive at the ultrasonic frequencies, around 100 kHz, produced by the arc discharges and are connected to tuned receivers and data processing unit 25 which will be described in further detail later and which determines the difference between mean time of receipt of an impulse at X (the average of the times of receipt at the two microphones 20, 21) and the mean time of receipt of the same impulse at Y (the average of the time of receipt at the microphones 22, 23). The difference between these mean times is the time interval taken for the shock wave to travel from X to Y. The velocity of the acoustic wave in the material depends on Young's modulus, Poisson's ratio and the relative density. Young's modulus is temperature-dependent and it is readily possible to calibrate empirically the output of the receiver and data processor in terms of the temperature of the strip in the region between X and Y. If the metal strip is being annealed, the magnitude of Young's modulus may depend on the proper annealing of the strip, which will depend on the correct temperature of treatment and the output of the receiver and data processor 25 may be utilised as an overall check on the annealing process to which the strip has been subjected.

By utilising pairs of receiving microphones 20, 21 and 22, 23, the two microphones in each pair being located near opposite faces of the strip, and averaging the time of receipt of the shock wave at the two microphones of the pair, the apparatus can function satisfactorily despite transverse movements of the strip, that is to say movements towards one microphone and away from the other in a pair. It is thus possible to utilise this form of testing apparatus as a non-contact monitor of temperature or other physical properties of a metal strip which is moving at high speed and which therefore may be subject to oscillation in directions normal to the plane of the strip.

Preferably directional microphones are employed to ensure pick-up of the acoustic waves from a localised area of the strip. The microphones and receiver may be arranged to operate preferentially at a desired frequency, for example to receive ultrasonic radiation, preferably with a high-pass filter to cut out noise.

The unit 25 is shown in further detail in FIG. 2. The inputs from the four microphones 20, 21, 22, 23 are fed respectively to four tuned amplifiers 30, 31, 32, 33 which amplify and filter the signals of around 100 kHz and give detected outputs. These outputs are passed to respective threshold comparators 34, 35, 36, 37 which cut off the lower level part of the signal, which is primarily noise. The signal from the spark gap, as an electric pulse from the generator 12, is applied to a trigger circuit 38 which is essentially a waveform generator. The output from this trigger circuit, after passing through a delay 39 provides a first output on a lead 40 for starting an electronic timer 41 counting clock pulses from a clock 42. The output from the delay circuit 39 is also used to open gates 43, 44, 45, 46 for admitting the outputs from the comparators to the timer 41. These gates have respective associated delays 47, 48, 49, 50. The various delays conveniently are digital counters and they are such that the gates open only at the appropriate times after the spark gap has been energised in order to reduce interference in the timer from any spurious signals which might be picked up by the microphones. The gated received signals are fed to the timer 41 on leads 51, 52, 53, 54. The timer 41 determines the times of arrival (measured from the time of spark discharge) at each of the four microphones and gives these outputs, in digital form on four leads 57, 58, 59, 60 (corresponding respectively to the times at microphones 20, 21, 22, 23). The outputs on leads 57, 58 are applied to an adder 61 and the outputs on leads 59, 60 are applied to another adder 62. The summed output of adder 61 is subtracted from that of adder 62 in a subtractor 63 to give the required mean time of transit from the location of microphones 20, 21 to the location of microphones 22, 23. This mean time is fed to a programmed calculator 64 having inputs of m, $\sigma$ and $\rho$ on leads 65, 66, 67 respectively and which determines Young's modulus E indicated on an indicator 68.

Figure 3:
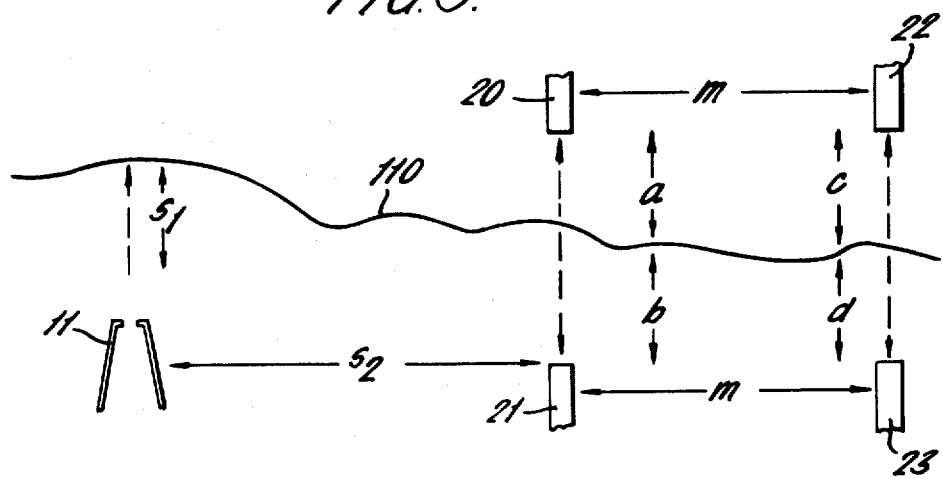
FIG. 3 is an explanatory diagram.

Mechanical movement of the strip may generate acoustic waves but these would be low frequency signals outside the filtered frequency range. The arrangement described above compensates for any changes in distance from the microphones due to transverse movement of the strip. Referring to FIG. 3, the instantaneous position of the strip is shown at 110, with exaggerated transverse displacements. The time taken for a signal to travel from the spark to a microphone is measured by the circuit just described. The signal travels to the microphones 20-23 from spark 11. The measurement time is of the order of microseconds and so compared to the speed of the signal and at the moment of measurement, the strip appears to be stationary. By the time the signal is measured again (next d.c. pulse) about 20 ms will have elapsed and the strip will have moved, i.e. the strip moves position between successive signal pulses but its movement is too slow to have any effect during a single pulse. Since all measurements are taken during a single pulse, the strip movement can be ignored.

Assume the four microphones 20, 21, 22, and 23 are respectively at distances a, b, c and d from the strip at the moment of measurement. The arc is a distance $s_1$ from the strip and $s_2$ from the nearest microphone, and the microphones 20, 21, 22, 23 are a distance, m, apart. The spark signal takes a time ta to reach microphone 20, tb to reach 21, tc to reach 22 and td to reach 23. So in time ta the signal travels a distance $(s_1+s_2+a)$ and in time tb, it travels $(s_1+s_2+b)$ and so on. Thus the time $(ta+tb)$ is proportional to $2(s_1+s_2)+(a+b)$.

Similarly the signals travel to 23 in time tc through a distance $(s_1+s_2+m+c)$. So $(tc+td)$ is proportional to $2(s_1+s_2+m)+(c+d)$. By subtracting $(ta+tb)$ from $(tc+td)$, we have $$\{2(s_1+s_2+m)-2(s_1+s_2)-(a+b)-(c+d)\}$$

as the total distance travelled in time $(tc+td)-(ta+tb)$. The microphones are in fixed positions so that $(a+b)$ is the same distance as $(c+d)$. Thus the total distance travelled is simply 2 m, i.e. twice the distance between the fixed microphones and independent of the strip movement.

The timer 41 gives four time signals, ta, tb, tc, td, which are then subtracted $(tc+td)-(ta+tb)$ and the resultant time, T, is related to the distance between the microphones, m, by the equation, $V=(2m/T)$ where V is the ultrasonic velocity in the strip. Young's modulus is obtained from this from the equation:

$$V = \left( \frac{E}{2(1+\sigma)\rho} \right)^{\frac{1}{2}}$$

where
E is Young's modulus
$\sigma$ is Poisson's ratio
$\rho$ is strip density.

I claim:

1. A method of determining a parameter representative of a physical property of continuously moving metal strip comprising the steps of generating an acoustical shock wave, containing ultrasonic frequencies, near one location on the surface of the strip and measuring the time of transmission of the shock wave through the strip between second and third locations to enable the velocity of propagation to be determined, wherein the time of arrival of the acoustic shock wave at each of said second and third locations in the material is determined by using, for each of said second and third locations, two microphones near but not in contact with opposite faces of the strip and determining the difference between the mean arrival times of the acoustic wave at the two microphones at the second and third locations.

2. A method as claimed in claim 1 wherein said acoustical shock wave is generated by a spark discharge.

3. Apparatus for determining a parameter representative of a physical property of continuously moving metal strip comprising a shock wave generator near one surface of the strip at one fixed location for generating a shock wave containing ultrasonic frequencies and, at each of spaced second and third fixed locations, two acoustic signal receivers near the strip but on opposite faces thereof and means responsive to the difference between the average time of receipt of the shock wave at the two receivers at the second location and the average time of receipt at the two receivers at the third location for determining the velocity of propagation of the acoustic wave signal between the second and third locations in the strip under test.

4. Apparatus as claimed in claim 3 wherein the shock wave generator comprises means producing an electric spark to provide a short duration pulse signal.

5. Apparatus as claimed in claim 4 wherein the shock wave generator is arranged to provide repetitive sparks giving repetitive short duration pulse signals.

6. Apparatus as claimed in claim 3 and having a collimator between the shock wave generator and said material to direct the shock wave onto a selected surface region of the material.

7. Apparatus as claimed in claim 3 wherein each receiver is a microphone near the surface of the material.

8. Apparatus as claimed in claim 7 wherein each microphone is a directional microphone.

9. Apparatus as claimed in claim 7 wherein a collimator is provided between the material and the microphone.

10. Apparatus as claimed in claim 3, and having a counter for determining the time of receipt of signals at the various microphones measured from the time of operation of the shock wave generator.

11. Apparatus as claimed in claim 10 wherein gating circuits are provided for controlling the application of signals to said counter, said gating circuits include delays so that they are open for predetermined periods after the operation of the shock wave generator.

* * * * *